US008697111B2

(12) United States Patent
Desai et al.

(10) Patent No.: US 8,697,111 B2
(45) Date of Patent: Apr. 15, 2014

(54) OSTEOCHONDRAL IMPLANT COMPRISING OSSEOUS PHASE AND CHONDRAL PHASE

(75) Inventors: Arpan Desai, Hamden, CT (US); Timothy Sargeant, Hamden, CT (US); Atu Agawu, Princeton, NJ (US); Joshua Stopek, Yalesville, CT (US)

(73) Assignee: Covidien LP, Mansfield, MA (US)

( * ) Notice: Subject to any disclaimer, the term of this patent is extended or adjusted under 35 U.S.C. 154(b) by 65 days.

(21) Appl. No.: 12/778,256

(22) Filed: May 12, 2010

(65) Prior Publication Data

US 2011/0282465 A1 Nov. 17, 2011

(51) Int. Cl.
*A61F 2/00* (2006.01)
*C12N 11/02* (2006.01)
*C12N 11/08* (2006.01)
*C12N 11/06* (2006.01)
*C12N 11/04* (2006.01)
*G01N 33/544* (2006.01)
*G01N 33/545* (2006.01)
*G01N 33/549* (2006.01)
*C07K 17/02* (2006.01)
*C07K 17/08* (2006.01)
*C07K 17/06* (2006.01)
*C07K 17/04* (2006.01)

(52) U.S. Cl.
USPC ........... 424/423; 435/177; 435/180; 435/181; 435/182; 436/528; 436/531; 436/532; 436/535; 530/812; 530/815; 530/816; 530/817

(58) Field of Classification Search
None
See application file for complete search history.

(56) References Cited

U.S. PATENT DOCUMENTS

| | | | |
|---|---|---|---|
| 4,268,639 A | 5/1981 | Seidel et al. | |
| 4,359,049 A | 11/1982 | Redl et al. | |
| 4,631,055 A | 12/1986 | Redl et al. | |
| 4,735,616 A | 4/1988 | Eibl et al. | |
| 4,874,368 A | 10/1989 | Miller et al. | |
| 4,902,281 A | 2/1990 | Avoy | |
| 4,932,942 A | 6/1990 | Maslanka | |
| 4,978,336 A | 12/1990 | Capozzi et al. | |
| 5,116,315 A | 5/1992 | Capozzi et al. | |
| 5,162,430 A | 11/1992 | Rhee et al. | |
| 5,306,500 A | 4/1994 | Rhee et al. | |
| 5,324,775 A | 6/1994 | Rhee et al. | |
| 5,410,016 A | 4/1995 | Hubbell et al. | |
| 5,514,379 A | 5/1996 | Weissleder et al. | |
| 5,543,441 A | 8/1996 | Rhee et al. | |
| 5,550,187 A | 8/1996 | Rhee et al. | |
| 5,752,974 A | 5/1998 | Rhee et al. | |
| 5,842,477 A * | 12/1998 | Naughton et al. | 128/898 |
| 5,861,043 A | 1/1999 | Carn | |
| 5,874,500 A | 2/1999 | Rhee et al. | |
| 5,947,893 A * | 9/1999 | Agrawal et al. | 600/36 |
| 6,152,943 A | 11/2000 | Sawhney | |
| 6,179,862 B1 | 1/2001 | Sawhney | |
| 6,514,534 B1 | 2/2003 | Amarpreet | |
| 6,566,406 B1 | 5/2003 | Chandrashekhar | |
| 6,605,294 B2 | 8/2003 | Amarpreet | |
| 6,656,200 B2 | 12/2003 | Li et al. | |
| 6,673,093 B1 | 1/2004 | Sawhney | |
| 6,703,047 B2 | 3/2004 | Amarpreet | |
| 6,818,018 B1 | 11/2004 | Amarpreet | |
| 7,009,034 B2 | 3/2006 | Chandrashekhar | |
| 7,347,850 B2 | 3/2008 | Amarpreet | |
| 7,427,293 B2 * | 9/2008 | Nycz et al. | 623/14.12 |
| 7,572,291 B2 * | 8/2009 | Gil et al. | 623/14.12 |
| 7,824,701 B2 * | 11/2010 | Binette et al. | 424/423 |
| 7,935,363 B2 * | 5/2011 | Ratcliffe | 424/443 |
| 2001/0046476 A1 | 11/2001 | Plochocka | |
| 2003/0108511 A1 | 6/2003 | Sawhney | |
| 2004/0185250 A1 | 9/2004 | John | |
| 2005/0043814 A1 | 2/2005 | Kusanagi et al. | |
| 2005/0281883 A1 | 12/2005 | Daniloff et al. | |
| 2005/0282997 A1 | 12/2005 | Ward et al. | |
| 2007/0100449 A1 | 5/2007 | O'Neil et al. | |
| 2008/0114092 A1 | 5/2008 | Amarpreet | |
| 2008/0200586 A1 | 8/2008 | Holden et al. | |
| 2009/0028957 A1 | 1/2009 | Daniloff | |
| 2009/0098183 A1 * | 4/2009 | Detamore et al. | 424/423 |
| 2009/0105366 A1 | 4/2009 | Vogt et al. | |
| 2009/0148487 A1 * | 6/2009 | Siedler et al. | 424/422 |

FOREIGN PATENT DOCUMENTS

| | | |
|---|---|---|
| EP | 2 143 737 A1 | 1/2010 |
| EP | 2 196 193 A1 | 6/2010 |
| EP | 2 233 160 A2 | 9/2010 |
| EP | 2 233 161 A2 | 9/2010 |
| FR | 2839451 A1 | 11/2003 |

OTHER PUBLICATIONS

International Search Report issued in Application EP 11250562.3 mailed Dec. 8, 2011.
International Search Report issued in Application EP 11250564.9 mailed Dec. 8, 2011.
International Search Report issued in Application EP 11250563.1 mailed Dec. 27, 2011.
International Search Report issued in Application EP 11250566.4 mailed Dec. 22, 2011.
International Search Report issued in Application EP 11250565.6 mailed Dec. 23, 2011.
Raul Zurita et al.: "Triclosan Release from Coated Polyglycolide Threads", Macromolecular Bioscience, vol. 6, No. 1, Jan. 5, 2006, pp. 58-69.
European Search Report for EP 07751966 date of completion is Nov. 5, 2012.
International Search Report from application EP 10251719.0 mailed May 24, 2013.

* cited by examiner

*Primary Examiner* — David M Naff

(57) ABSTRACT

An osteochondral plug includes a first scaffold and a second scaffold. The first scaffold may be a solid scaffold containing one or more pendant reactive functional groups. The second scaffold capable of reacting with the one or more pendant reactive functional groups of the first scaffold.

13 Claims, 2 Drawing Sheets

OSTEOCHONDRAL IMPLANT COMPRISING OSSEOUS PHASE AND CHONDRAL PHASE

TECHNICAL FIELD

The present disclosure relates to methods and devices for the treatment of tissue defects. More particularly, the present disclosure relates to biphasic osteochondral plugs and methods of forming and using the same in the treatment of osteochondral defects.

BACKGROUND

Osteochondral defects are combination lesions of the bone and cartilage. Particularly, osteochondral defects affect the joints, such as the knee, ankle, shoulder, and elbow, and include lesions to both the articular cartilage and underlying subchondral bone. Treatment options include filling the defect with a bone or cartilage filler, as well as allograft or autograph transplantation of cells/tissue.

Current void filling devices include hydrogels, sponges, scaffolds, and cements. The limitation with these devices, however, is that they are single phase. Single phase void fillers cannot cater to the needs of a void having more than one tissue type. Solid layered plugs have also been utilized to fill voids; however, these plugs may leave gaps between the tissue and the implanted device.

It would be advantageous to provide a biphasic, or multiphasic, plug tailored to specific tissue types by customizing the physical properties of each phase to accommodate the biomechanical properties of each tissue type, as well as optimizing the biochemical compatibility of each phase to its respective tissue type to favor growth and repair of the distinct tissues.

SUMMARY

The present osteochondral plugs include a first scaffold and a second scaffold. The first scaffold is a solid scaffold containing pendant reactive functional groups. The second scaffold includes a hydrogel capable of reacting with the pendant reactive groups of the first scaffold. The first scaffold may be porous. In embodiments, the first scaffold may be a sponge, or foam.

The second scaffold includes at least one hydrogel precursor. In embodiments, the at least one precursor is an electrophile or a nucleophile. In other embodiments, the second scaffold includes at least two precursors. The at least two precursors may include an electrophile and a nucleophile. In embodiments, the nucleophile is a natural component. In embodiments, the at least two precursors include a PEG star and collagen. In other embodiments, the at least two precursors include a PEG star and NHS. The term PEG star is meant to include a multibranched molecule which contains polyethylene glycol segments.

The first and second scaffolds may be designed to interact with one another to form covalent bonds. In addition, the first and second scaffolds may be designed to interact with the tissue to also form covalent bonds between the plug and the tissue.

Methods of filling an osteochondral defect with the osteochondral plugs of the present disclosure are also provided. In accordance with an embodiment of the present methods, an osseous scaffold may be placed within a tissue defect and a hydrogel may be injected into the tissue defect over the osseous scaffold. The osseous scaffold may be loaded into a delivery device prior to placement of the osseous scaffold in the tissue defect. The delivery device includes an outer shaft having an inner channel for housing the osseous scaffold. A plunger, optionally including a central bore, is adapted for slidable engagement with the inner channel for driving the osseous scaffold into the tissue defect. The osseous scaffold may then be ejected from the delivery device. The hydrogel may be injected into the tissue defect by introducing the hydrogel into the defect through the central bore of the plunger of the delivery device.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
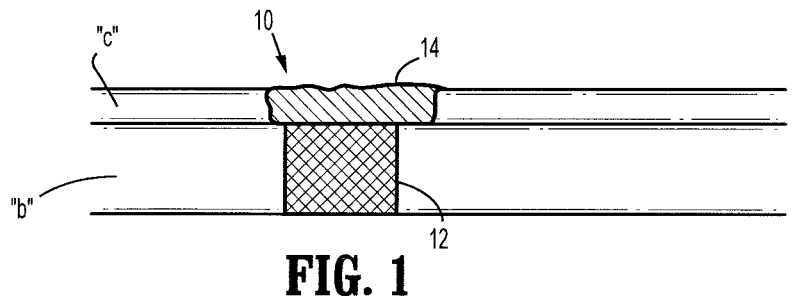
FIG. 1 schematically shows an osteochondral plug placed within an osteochondral defect in accordance with one embodiment of the present disclosure.

Osteochondral plugs in accordance with the present disclosure are at least biphasic and include a first, osseous phase and a second, chondral phase. Upon implantation, the first phase promotes bone repair by favoring the growth of osteogenic cell types and providing similar mechanical properties to that of bone. The second phase promotes cartilage repair by favoring the growth of chondrogenic cell types and providing similar mechanical properties to that of cartilage.

The first osseous phase may include a first scaffold, at least a portion of which includes one or more pendant reactive groups. By pendant, the one or more reactive groups may be positioned at or near a surface of the scaffold in a manner conducive for interaction with the tissue and/or the second chondral phase of the plug.

The second chondral phase may include a second scaffold, at least a portion of which includes one or more pendant complimentary reactive groups. The one or more pendant complimentary reactive groups of the second scaffold are capable of covalently bonding with the one or more pendant reactive groups of the first scaffold and/or the tissue to form a multiphase osteochondral plug.

The multiphase osteochondral plugs may be used in a variety of surgical and wound applications involving defects of two or more tissue types. As used herein, a "tissue defect" may include any breakdown of tissue from a normal, healthy state. This breakdown may be due to internal factors such as degenerative disease, or external factors such as injury. Any variation from the normal structure of a tissue may be a "tissue defect." Thus, the osteochondral plugs of the present disclosure may be used to fill voids as a tissue filler, bone filler, or filler for soft/hard tissue interfaces; to promote tissue growth as a tissue scaffold; and/or to deliver bioactive agents and/or cells to a tissue defect or lesion.

The Osseous Phase

The osseous phase of the osteochondral plug of the present disclosure includes a first scaffold or structure upon, or within, which the desired osteogenic cells may grow in order to regenerate the desired tissue. At least a portion of the first scaffold may include one or more pendant reactive functional groups suitable for interacting with the tissue and/or the chondral phase of the plugs described herein. The osseous phase may be in the form of a rod, cylinder, sponge, foam, gel, or any other desired configuration that provides both a structure having the necessary strength to support the defect, as well as a structure upon or within which the desirable cells may grow. The osseous phase may be provided as a composition in liquid form which hardens to form a solid scaffold. The composition may harden in vivo or in vitro, prior to or after, implantation in tissue.

In embodiments, the osseous phase may include a porous scaffold. The term "porous" as used herein means that the scaffold or structure may possess defined openings and/or spaces which are present as a surface characteristic or a bulk material property, partially or completely penetrating the scaffold. Pores may be created using any method within the purview of those skilled in the art including, but not limited to, processes such as sintering, lyophilization, leaching of salt, and sugar or starch crystals, or the addition of gas-forming agents (i.e., sodium bicarbonate), or the addition of gas-filled microbubbles. Porous scaffolds may have an open-cell structure, where the pores may be connected to each other, forming an interconnected network. Conversely, the porous scaffolds may include pores which are not interconnected.

In some embodiments, the pores may be formed after implantation in situ. The in situ pore formation may be performed using any suitable method. Some non-limiting examples include the use of contact lithography, living radical photopolymer (LRPP) systems, and salt leaching. Those skilled in the art reading the present disclosure will envision other pore distribution patterns and configurations for the osseous phase.

In some embodiments, the first scaffold may be a foam or a sponge containing openings or pores over at least a portion of a surface thereof, upon and within which desired cells may grow. The foam or sponge may be formed using any suitable method including, but not limited to the lyophilization or freeze-drying of a composition. The foam or sponge may be cross-linked or non-cross-linked, and may include covalent or ionic bonds.

The first scaffold of the osseous phase may be fabricated from any biodegradable or non-biodegradable polymer that can be used in surgical procedures. The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. It should be understood that such materials include natural, synthetic, bioabsorbable, and/or non-absorbable materials, as well as combinations thereof, for forming the osseous phase of the present disclosure.

Representative natural biodegradable polymers include: polysaccharides, such as alginate, dextran, chitin, chitosan, hyaluronic acid (HA), cellulose, fucans, glycosaminoglycans, and chemical derivatives thereof (substitutions and/or additions of chemical groups, for example, alkyl, alkylene, hydroxylations, oxidations, and other modifications routinely made by those skilled in the art); and poly(amino acids) including proteins, such as albumin, casein, zein, silk, collagen (I, II, and III), elastin, fibrin, fibrinogen, gelatin, and copolymers and blends thereof, alone or in combination with synthetic biodegradable polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These may be collectively referred to herein, in embodiments, as "celluloses."

Representative synthetic biodegradable polymers include polyhydroxy acids prepared from lactone monomers, such as glycolide, lactide, caprolactone, $\epsilon$-caprolactone, valerolactone, and $\delta$-valerolactone, as well as carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-($\epsilon$-caprolactone)); poly(glycolide-co-($\epsilon$-caprolactone)); poly(lactic-co-glycolic acid); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Other non-limiting examples of biodegradable materials from which the osseous phase may be made include: poly(phosphazine); aliphatic polyesters; polyethylene glycols; glycerols; copoly (ether-esters); polyalkylene oxalates; polyamides; poly (iminocarbonates); polyalkylene oxalates; polyoxaesters; polyphosphazenes; and copolymers, block copolymers, homopolymers, blends, and combinations thereof.

Rapidly bioerodible polymers, such as poly(lactide-co-glycolide)s, polyanhydrides, and polyorthoesters, which have carboxylic groups exposed on the external surface as the surface of the polymer erodes, may also be used.

Some non-limiting examples of suitable nondegradable materials from which the osseous phase may be made include polyolefins, such as polyethylene and polypropylene including atactic, isotactic, syndiotactic, and blends thereof, polyethylene glycols, polyethylene oxides, ultra high molecular weight polyethylene, copolymers of polyethylene and polypropylene, as well as, polyisobutylene and ethylene-alphaolefins copolymers, and fluorinated polyolefins such as polytetrafluoroethylene; polyamides such as nylon and polycaprolactam; polyamines; polyimines; polyesters such as polyethylene terephthalate and polybutylene terephthalate; aliphatic polyesters; polytetrafluoroethylene; polyethers; polyether-esters such as polybutester; polytetramethylene ether glycol; 1,4-butanediol; polyurethanes; acrylic polymers and copolymers; modacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polyacrylonitrile; polyvinyl ketones; polyvinyl aromatics such as polystyrene; polyvinyl esters such as polyvinyl acetate; copolymers of vinyl monomers with each other and olefins such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, and combinations thereof.

The biodegradable materials may be crosslinked with a crosslinking agent to enhance the mechanical strength of the osseous phase. Crosslinking agents are within the purview of those skilled in the art, and include, for example, calcium salts such as hydroxyapatite; aldehyde crosslinking agents such as glutaraldehyde; isocyanate crosslinking agents such as hexamethylene diisocyanate; carbodiimide crosslinking agents such as 1-ethyl-3-(3-dimethylaminopropyl) carbodiimide hydrochloride; polyepoxy crosslinking agents such as ethylene glycol diglycidyl ether; and transglutaminase.

At least a portion of the first scaffold may include one or more pendant reactive functional groups suitable for interacting with the tissue and/or the chondral phase of the plugs described herein. The term "reactive functional group" as used herein refers to electrophilic or nucleophilic groups capable of reacting with each other to form a bond. Electrophilic functional groups include, for example, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In certain embodiments, the electrophilic functional group is a succinimidyl ester.

Suitable nucleophilic groups which may be present on at least a portion of the first scaffold surface include, but are not limited to, —$NH_2$, —SH, —OH, —$PH_2$, —CO—NH—$NH_2$ and combinations thereof.

It is contemplated by the present disclosure that the functional groups may be the same or different at each occurrence. Thus, the first scaffold may have two different electrophilic groups, or two different nucleophilic groups.

The reactive groups may be positioned on or near the surface of the first scaffold using any suitable manner. For example, the first scaffold may be formed from materials which naturally position reactive groups toward the outer surface of the scaffold. In other examples, the first scaffold may be surface-modified to covalently attach the reactive groups. In still other examples, the first scaffolds may be coated with an additional layer of material which includes the pendant reactive groups necessary to interact with the tissue and/or the second phase of the plugs described herein.

In some embodiments, the coating process includes surface treatment of the osseous phase in order to promote adhesion of the coating to the surface of the osseous phase. The surface of the osseous phase can be treated using plasma, physical or chemical vapor deposition, pulsed laser ablation deposition, surface modification, or any other means within the purview of those skilled in the art to activate the surface of the osseous phase with the amine-functionalized coating. In other embodiments, treatment may include the use of a primer such as a cross-linkable compound. In yet other embodiments, one or more deposition treatments could be used alone or in conjunction with the primer to achieve the desired association of amine-functionalized coating with the osseous phase.

In embodiments, the osseous phase includes a first scaffold made from bone cement. For example, the first scaffold may be made from a poly(methyl methacrylate). In certain embodiments, the first scaffold may be made from a two-component material which includes an aminated poly(methyl methacrylate) powder which can be mixed with a liquid methyl methacrylate monomer. An accelerator, such as for example, N,N-dimethyl-p-toluidine, N,N-dimethylaniline, N,N-bis(2-hydroxylethyl)-p-toluidine, and organic copper (II) salts, may be used to initiate free radical polymerization of the monomer. The two-component material may be molded to fit the tissue defect and allowed to harden to match the mechanical properties of the bone. In some embodiments, the two-part material may be hardened in the tissue defect. In other embodiments, the two-part material may be hardened prior to implantation.

The Chondral Phase

The chondral phase of the osteochondral plug of the present disclosure includes a second scaffold or structure upon, or within, which desired cartilage cells may grow in order to regenerate the desired tissue. The second scaffold being capable of reacting with the one or more pendant reactive groups of the first scaffold to form a bond. In embodiments, the second scaffold may be porous.

The second scaffold may include at least hydrogel precursor suitable for forming a hydrogel material. At least one of the hydrogel precursors of the chondral phase may be capable of reacting with the pendant reactive groups of the osseous phase. The hydrogel precursor may be, e.g., a monomer or a macromer. The hydrogel precursor may be a solid or a liquid. One type of precursor may have a reactive functional group that is an electrophile or a nucleophile. Electrophiles react with nucleophiles to form covalent bonds. Covalent crosslinks or bonds refer to chemical groups formed by reaction of functional groups on different materials that serve to covalently bind the different materials to each other. In certain embodiments, a first set of electrophilic functional groups on a first precursor may react with a second set of nucleophilic functional groups on a second precursor. When the precursors are mixed in an environment that permits reaction (e.g., as relating to pH or solvent), the functional groups react with each other to form covalent bonds. The precursors become crosslinked when at least some of the precursors can react with more than one other precursor. For instance, a precursor with two or more functional groups of a first type may be reacted with a crosslinking precursor that has two or more functional groups of a second type capable of reacting with the first type of functional groups.

The hydrogel may be formed from single or multiple precursors. For example, where the hydrogel is formed from multiple precursors, for example two precursors, the precursors may be referred to as a first and a second hydrogel precursor. The terms "first hydrogel precursor" and "second hydrogel precursor" each are meant to include any of a polymer, functional polymer, macromolecule, small molecule, or crosslinker that can take part in a reaction to form a network of crosslinked molecules, e.g., a hydrogel.

The term "reactive functional group" as used herein refers to electrophilic or nucleophilic groups capable of reacting with each other to form a bond. Electrophilic functional groups include, for example, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In embodiments, the electrophilic functional group is a succinimidyl ester.

As noted above, the present disclosure provides hydrogels which include an electrophilic precursor, sometimes referred to herein as an electrophilic crosslinker, and a nucleophilic component. In embodiments, the nucleophilic component is a natural component, which may be cross-linked by the electrophilic crosslinker to form a hydrogel. In embodiments, the hydrogel may be biodegradable.

The hydrogel may be formed prior to implantation or may be formed in situ at the time of implantation. The components for forming hydrogels on or in tissues may include, for example, in situ forming materials. When formed in situ, the hydrogels may conform to the surface geometry of the osseous phase, mechanically interlocking with the osseous phase. The in situ forming material may include a single precursor or multiple precursors that form "in situ," meaning formation occurs at a tissue in a living animal or human body. In general, this may be accomplished by having a precursor that can be activated at the time of application to create, in embodiments, a hydrogel. Activation can be through a variety of methods including, but not limited to, environmental changes such as pH, ionicity, temperature, ultraviolet light (UV), etc. In other embodiments, the components for forming a hydrogel may be contacted outside the body and then introduced into a patient as an implant such as a (pre-formed) tissue scaffold.

In some embodiments, as discussed further below, the hydrogel itself may include a natural component such as collagen, gelatin, hyaluronic acid, combinations thereof, and the like. In certain embodiments the natural component may be released at the site of implantation as the hydrogel degrades. The term "natural component" as used herein includes polymers, compositions of matter, materials, combinations thereof, and the like, which can be found in nature or derived from compositions/organisms found in nature. Natural components also may include compositions which are found in nature but can be synthesized by man, for example, using methods to create natural/synthetic/biologic recombinant materials, as well as methods capable of producing proteins with the same sequences as those found in nature, and/or methods capable of producing materials with the same structure and components as natural materials, such as synthetic hyaluronic acid, which is commercially available, for example, from Sigma Aldrich.

The hydrogel precursors, e.g., the electrophilic hydrogel precursors, may have biologically inert and water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); polysaccharides such as dextran, chitosan, alginates, chitin, carboxymethylcellulose, oxidized cellulose, hydroxyethylcellulose, and hydroxymethylcellulose; hyaluronic acid (HA); and poly(amino acids) including proteins such as albumin, collagen (I, II, and III), elastin, fibrin, fibrinogen, casein, and gelatin. Other suitable hydrogels may include components such as methacrylic acid, acrylamides, methyl methacrylate, hydroxyethyl methacrylate, combinations thereof, and the like. In embodiments, combinations and components of the foregoing polymers may be utilized.

The polyethers, and more particularly poly(oxyalkylenes) or poly(ethylene glycol) or polyethylene glycol, may be utilized in some embodiments. When the core is small in molecular nature, any of a variety of hydrophilic functionalities can be used to make the first and second hydrogel precursors water soluble. For example, functional groups like hydroxyl, amine, sulfonate and carboxylate, which are water soluble, may be used to make the precursor water soluble. For example, the n-hydroxysuccinimide ("NHS") ester of subaric acid is insoluble in water, but by adding a sulfonate group to the succinimide ring, the NHS ester of subaric acid may be made water soluble, without affecting its reactivity towards amine groups. In embodiments, the precursor having electrophilic functional groups may be a PEG ester.

As noted above, each of the first and second hydrogel precursors may be multifunctional, meaning that it may include two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form cross-linked polymeric products.

A macromolecule having the electrophilic functional group may be multi-armed. For example, the macromolecule may be a multi-armed PEG having four, six, eight, or more arms extending from a core. The core may be the same or different from the macromolecule forming the arms. For example, the core may be PEG and the multiple arms may also be PEG. In embodiments, the core may be a natural polymer.

The molecular weight (MW) of the electrophilic crosslinker may be from about 2,000 to about 100,000; in embodiments from about 10,000 to about 40,000. Multi-arm precursors may have a molecular weight that varies depending on the number of arms. For example, an arm having a 1000 MW of PEG has enough $CH_2CH_2O$ groups to total at least 1000 MW. The combined molecular weight of an individual arm may be from about 250 to about 5,000; in embodiments from about 1,000 to about 3,000; in embodiments from about 1,250 to about 2,500. In embodiments, the electrophilic crosslinker may be a multi-arm PEG functionalized with multiple NHS groups having, for example, four, six or eight arms and a molecular weight from about 5,000 to about 25,000. Other examples of suitable precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated herein by reference.

The electrophilic precursor may be a cross-linker that provides an electrophilic functional group capable of bonding with nucleophiles on another component, in embodiments a natural component. The natural component may be endogenous to the patient to which the electrophilic crosslinker is applied, or may be exogenously applied.

In embodiments, one of the precursors may be a natural component possessing nucleophilic groups. Nucleophilic groups which may be present include, for example, —$NH_2$, —SH, —OH, —$PH_2$, and —CO—NH—$NH_2$. Any monomer, macromer, polymer, or core described above as suitable for use in forming the electrophilic precursor may be functionalized with nucleophilic groups to form a nucleophilic precursor. In other embodiments, a natural component possessing nucleophilic groups may be utilized as the nucleophilic precursor.

The natural component may be, for example, collagen, gelatin, blood (including serum, which may be whole serum or extracts therefrom), hyaluronic acid, proteins, albumin, other serum proteins, serum concentrates, platelet rich plasma (prp), chondroitin sulfate, combinations thereof, and the like. Additional suitable natural components which may be utilized or added to another natural component, sometimes referred to herein as a bioactive agent, include, for example, stem cells, DNA, RNA, enzymes, growth factors, peptides, polypeptides, antibodies, other nitrogenous natural molecules, combinations thereof, and the like. Other natural components may include derivatives of the foregoing, for example modified hyaluronic acid, dextran, other polysaccharide, polymers and/or polypeptides, including aminated polysaccharides which may be naturally derived, synthetic, or biologically derived. For example, in embodiments hyaluronic acid may be modified to make it nucleophilic.

In embodiments, any of the above natural components may be synthetically prepared, e.g., synthetic hyaluronic acid, utilizing methods within the purview of those skilled in the art. Similarly, in embodiments the natural component could be a natural or synthetic long chain aminated polymer. The natural component may also be modified, i.e., aminated to create a nucleophilic polymer.

The natural component may provide cellular building blocks or cellular nutrients to the tissue that it contacts in situ. For example, serum contains proteins, glucose, clotting factors, mineral ions, and hormones which may be useful in the formation or regeneration of tissue.

In embodiments, the natural component includes whole serum. In embodiments, the natural component is autologous, i.e., collagen, serum, blood, and the like, from the body where the hydrogel is (or is to be) formed. In this manner, the person or animal in which the hydrogel is to be used may provide the natural component for use in formation of the hydrogel. In such embodiments, the resulting hydrogel is semi-autologous, including a synthetic electrophilic precursor and an autologous/endogenous nucleophilic precursor.

In embodiments, a multifunctional nucleophilic polymer, such as a natural component having multiple amine groups, may be used as a first hydrogel precursor and a multifunctional electrophilic polymer, such as a multi-arm PEG functionalized with multiple NHS groups, may be used as a second hydrogel precursor. In embodiments, the precursors may be in solution(s), which may be combined to permit formation of the hydrogel. Any solutions utilized as part of the in situ forming material system should not contain harmful or toxic solvents. In embodiments, the precursor(s) may be substantially soluble in a solvent such as water to allow application in a physiologically-compatible solution, such as buffered isotonic saline.

In embodiments, a hydrogel may be formed from collagen, or a combination of collagen and/or gelatin, as the natural component, with a multi-functional PEG utilized as a crosslinker. In embodiments, the collagen and/or gelatin may be placed in solution, utilizing a suitable solvent. To this solution, hyaluronic acid may be added along with a high pH buffer. Such a buffer may have a pH from about 8 to about 12, in embodiments from about 8.2 to about 9. Examples of such buffers include, but are not limited to, borate buffers, and the like.

In a second solution, an electrophilic crosslinker, in embodiments a multi-arm PEG functionalized with electrophilic groups such as n-hydroxysuccinimide, may be prepared in a buffer such as Hanks Balanced Salt Solution, Dulbecco's Modified Eagle's Medium, Phosphate Buffered Saline, water, phosphate buffer, combinations thereof, and the like. The electrophilic crosslinker, in embodiments a multi-arm PEG functionalized with n-hydroxysuccinimide groups, may be present in a solution including the above buffer at a concentration from about 0.02 grams/ml to about 0.5 grams/ml, in embodiments from about 0.05 grams/ml to about 0.3 grams/ml.

The two components may be combined, in some embodiments upon introduction in situ, wherein the electrophilic groups on the multi-arm PEG crosslink the amine nucleophilic components of the collagen and/or gelatin. The ratio of natural component to electrophilic component (i.e., collagen: PEG) may be from about 0.1:1 to about 100:1, in embodiments from about 1:1 to about 10:1.

The nucleophilic components, in embodiments the natural components, e.g., collagen, gelatin, and/or hyaluronic acid, may together be present at a concentration of at least about 1.5 percent by weight of the hydrogel, in embodiments from about 1.5 percent by weight to about 20 percent by weight of the hydrogel, in other embodiments from about 2 percent by weight to about 10 percent by weight of the hydrogel. In certain embodiments, collagen may be present from about 0.5 percent to about 7 percent by weight of the hydrogel, in further embodiments, from about 1 percent to about 4 percent by weight of the hydrogel. In another embodiment, gelatin may be present from about 1 percent to about 15 percent by weight of the hydrogel, in further embodiments, from about 2 percent to about 15 percent by weight of the hydrogel. In yet another embodiment, hyaluronic acid and collagen combined as the natural component(s) may be present from about 0.5 percent to about 8 percent by weight of the hydrogel, in further embodiments, from about 1 percent to about 5 percent by weight of the hydrogel. It is also envisioned that the hyaluronic acid may not be present as a "structural" component, but as more of a bioactive agent. For example, hyaluronic acid may be present in solution/gel in concentrations as low as 0.001 percent by weight of the solution/gel and have biologic activity.

The electrophilic crosslinker may be present in amounts of from about 0.5 percent by weight to about 20 percent by weight of the hydrogel, in embodiments from about 1.5 percent by weight to about 15 percent by weight of the hydrogel.

Hydrogel materials may be formed either through covalent, ionic or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ, or as a consequence of a prevalent condition in the physiological environment, including: temperature, pH, ionic strength, combinations thereof, and the like. Chemical (covalent) crosslinking may be accomplished by any of a number of mechanisms, including: free radical polymerization, condensation polymerization, anionic or cationic polymerization, step growth polymerization, electrophile-nucleophile reactions, combinations thereof, and the like.

In some embodiments, hydrogel systems may include biocompatible multi-precursor systems that spontaneously crosslink when the precursors are mixed, but wherein the two or more precursors are individually stable for the duration of the deposition process. In other embodiments, in situ forming materials may include a single precursor that crosslinks with endogenous materials and/or tissues.

The crosslinking density of the resulting biocompatible crosslinked polymer may be controlled by the overall molecular weight of the crosslinker and natural component and the number of functional groups available per molecule. A lower molecular weight between crosslinks, such as 600 daltons (Da), will give much higher crosslinking density as compared to a higher molecular weight, such as 10,000 Da. Elastic gels may be obtained with higher molecular weight natural components with molecular weights of more than 3000 Da.

The crosslinking density may also be controlled by the overall percent solids of the crosslinker and natural component solutions. Increasing the percent solids increases the probability that an electrophilic group will combine with a nucleophilic group prior to inactivation by hydrolysis. Yet another method to control crosslink density is by adjusting the stoichiometry of nucleophilic groups to electrophilic groups. A one to one ratio may lead to the highest crosslink density, however, other ratios of reactive functional groups (e.g., electrophile:nucleophile) are envisioned to suit a desired formulation.

The hydrogel thus produced may be bioabsorbable, so that it does not have to be retrieved from the body. Absorbable materials are absorbed by biological tissues, and disappear in vivo at the end of a given period, which can vary, for example, from one day to several months, depending on the chemical nature of the material. Absorbable materials include both natural and synthetic biodegradable polymers, as well as bioerodible polymers.

In embodiments, one or more precursors having biodegradable linkages present in between functional groups may be included to make the hydrogel biodegradable or absorbable. In some embodiments, these linkages may be, for example, esters, which may be hydrolytically degraded in physiological solution. The use of such linkages is in contrast to protein linkages that may be degraded by proteolytic action. A biodegradable linkage optionally also may form part of a water soluble core of one or more of the precursors. Alternatively, or in addition, functional groups of precursors may be chosen such that the product of the reaction between them results in a biodegradable linkage. For each approach, biodegradable linkages may be chosen such that the resulting biodegradable biocompatible crosslinked polymer degrades or is absorbed in a desired period of time. Generally, biodegradable linkages may be selected that degrade the hydrogel under physiological conditions into non-toxic or low toxicity products.

Biodegradable gels utilized in the present disclosure may degrade due to hydrolysis or enzymatic degradation of the biodegradable region, whether part of the natural component or introduced into a synthetic electrophilic crosslinker. The degradation of gels containing synthetic peptide sequences will depend on the specific enzyme and its concentration. In some cases, a specific enzyme may be added during the crosslinking reaction to accelerate the degradation process. In the absence of any degradable enzymes, the crosslinked polymer may degrade solely by hydrolysis of the biodegradable segment. In embodiments in which polyglycolate is used as the biodegradable segment, the crosslinked polymer may degrade in from about 1 day to about 30 days depending on the crosslinking density of the network. Similarly, in embodiments in which a polycaprolactone based crosslinked network is used, degradation may occur over a period of time from about 1 month to about 8 months. The degradation time generally varies according to the type of degradable segment used, in the following order: polyglycolate<polylactate<polytrimethylene carbonate<polycaprolactone. Thus, it is possible to construct a hydrogel with a desired degradation profile, from a few days to months, using a proper degradable segment.

Where utilized, the hydrophobicity generated by biodegradable blocks such as oligohydroxy acid blocks or the hydrophobicity of PPO blocks in PLURONIC™ or TETRONIC™ polymers utilized to form the electrophilic crosslinker may be helpful in dissolving small organic drug molecules. Other properties which will be affected by incorporation of biodegradable or hydrophobic blocks include: water absorption, mechanical properties and thermosensitivity.

Certain properties of the hydrogel material can be useful, including adhesion to a variety of tissues, desirable setting times to enable a surgeon to accurately and conveniently place the hydrogel materials, high water content for biocompatibility, mechanical strength for use in implants, and/or toughness to resist destruction after placement. Synthetic materials that are readily sterilized and avoid the dangers of disease transmission involved in the use of natural materials may thus be used. Indeed, certain in situ polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200; 5,874,500; 5,543,441; 5,514,379; 5,410,016; 5,162,430; 5,324,775; 5,752,974; and 5,550,187.

As noted above, in embodiments a branched multi-arm PEG, sometimes referred to herein as a PEG star, may be included to form a hydrogel of the present disclosure. A PEG star may be functionalized so that its arms include pendant reactive biofunctional groups for biological signaling and/or molecular binding, such as amino acids, peptides, antibodies, enzymes, drugs, affinity binders, thiols, combinations thereof, or other moieties such as bioactive agents in its cores, its arms, or at the ends of its arms. The biofunctional groups may also be incorporated into the backbone of the PEG, or attached to a reactive group contained within the PEG backbone. The binding can be covalent or non-covalent, including electrostatic, thiol mediated, peptide mediated, or using known reactive chemistries, for example, biotin with avidin.

Amino acids incorporated into a PEG star may be natural or synthetic, and can be used singly or as part of a peptide. Sequences may be utilized for cellular adhesion, cell differentiation, combinations thereof, and the like, and may be useful for binding other biological molecules such as growth factors, drugs, cytokines, DNA, antibodies, enzymes, combinations thereof, and the like. Such amino acids may be released upon enzymatic degradation of the PEG star.

These PEG stars may also include functional groups as described above to permit their incorporation into a hydrogel. The PEG star may be utilized as the electrophilic crosslinker or, in embodiments, be utilized as a separate component in addition to the electrophilic crosslinker described above. In embodiments, the PEG stars may include electrophilic groups that bind to nucleophilic groups. As noted above, the nucleophilic groups may be part of a natural component utilized to form a hydrogel of the present disclosure.

In some embodiments a biofunctional group may be included in a PEG star by way of a degradable linkage, including an ester linkages formed by the reaction of PEG carboxylic acids or activated PEG carboxylic acids with alcohol groups on a biofunctional group. In this case, the ester groups may hydrolyze under physiological conditions to release the biofunctional group.

Optional Bioactive Agents

Bioactive agents may be added to the osteochondral plug of the present disclosure to provide specific biological or therapeutic properties thereto. Any product which may enhance tissue repair, limit the risk of sepsis, and modulate the mechanical properties of the osteochondral plug, or specific phase portion thereof, may be added during the preparation of the device or may be coated on the device. In embodiments, agents which may be added to the osteochondral plug include: fucans for antiseptic properties; chitosan and glutaraldehyde crosslinked collagen for their degradation time; and growth factors, peptides, proteins, drugs, and DNA for their tissue properties.

Moreover, the osteochondral plug may also be used for delivery of one or more bioactive agents. The bioactive agents may be incorporated into one or both of the phases of the osteochondral plug during formation of the device, such as by free suspension, liposomal delivery, microspheres, microbubbles, etc., or by coating a surface of the plug, or portion thereof, such as by polymer coating, dry coating, freeze drying, applying to a mesh surface, ionically, covalently, or affinity binding to functionalize the degradable components of the plug. Thus, in some embodiments, at least one bioactive agent may be combined with a phase of the osteochondral plug, i.e., the osseous phase and/or chondral phase, during formation to provide release of the bioactive agent during degradation of the plug. As the plug degrades or hydrolyzes in situ, the bioactive agents are released. In other embodiments, bioactive agents may be coated onto a surface or a portion of a surface of the osseous phase or chondral phase of the plug for quick release of the bioactive agent.

A bioactive agent as used herein is used in the broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect; a compound that affects or participates in tissue growth, cell growth, and/or cell differentiation; an anti-adhesive compound; a compound that may be able to invoke a biological action such as an immune response; or could play any other role in one or more biological processes. A variety of bioactive agents may be incorporated into the plug.

Examples of classes of bioactive agents, which may be utilized in accordance with the present disclosure include, for example, anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Other bioactive agents, which may be included as a bioactive agent include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; antihistamines; and immunological agents.

Other examples of suitable bioactive agents, which may be included in the osteochondral plug include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes. In some embodiments, peptides or antibodies may be used to bind growth factors to the plug.

It may be desirable to include bioactive agents which promote wound healing and/or tissue growth, including colony stimulating factors, blood proteins, fibrin, thrombin, fibrinogen, hormones and hormone analogs, blood coagulation factors, growth factors, bone morphogenic proteins, TGF-β, IGF, combinations thereof, and the like. In embodiments, the scaffold of either or both the osseous and chondral phases may deliver and/or release biological factors/molecules and/or cells at the site of implantation. Thus, it may assist in native tissue regrowth by providing the surrounding tissue with needed nutrients and bioactive agents.

As noted above, in embodiments that include a multi-arm PEG or PEG star, the bioactive agent may be incorporated into the core of the PEG, the arms of the PEG, or combinations thereof. In embodiments, the bioactive agent may be attached to a reactive group in the PEG chain. The bioactive agent may be bound covalently, non-covalently, i.e., electrostatically, through a thiol-mediated or peptide-mediated bond, or using biotin-avidin chemistries and the like.

In embodiments, the bioactive agent may be encapsulated by the hydrogel. For example, the hydrogel may form polymer microspheres around the bioactive agent. As the hydrogel hydrolyzes in situ, the bioactive components and any added bioactive agents are released. This may provide nutrients from the natural components, as well as bioactive agents, to the surrounding tissue, thereby promoting growth and/or regeneration of tissue.

Combining the Osseous and Chondral Phases

Various combinations of osseous and chondral phases may be used to fabricate the osteochondral plug according to the present disclosure. For example, any of the osseous phase materials and configuration as described above may be combined with any of the chondral phase hydrogels also described above, dependent upon the type of defect to be treated and the properties desired from the osteochondral plug.

The osseous phase may be a solid or cement-like scaffold which can become solid after a set cure time. Alternatively, the osseous phase may be a hydrogel that may be formed prior to implantation or in situ. The osseous phase should mimic the biomechanical properties of bone. In embodiments, the osseous phase is adapted to recruit and/or deliver endogenous growth factors, proteins, and/or cells. In embodiments, the material of the osseous phase includes reactive groups which may crosslink with the chondral phase.

The chondral phase may be a single or multi-component hydrogel containing water soluble biopolymers as at least one component. The precursor(s) of the hydrogel may be dissolved to form a solution prior to use, with the solution being delivered to the osteochondral defect. As used herein, a solution may be homogeneous, heterogeneous, phase separated, or the like. In other embodiments, the precursor(s) may be in an emulsion. Where two solutions are employed, each solution may contain one precursor of the hydrogel forming material which forms upon contact. The solutions may be separately stored and mixed when delivered to tissue.

In a single component system, the precursor, i.e., the electrophile, reacts with natural components of the tissue environment to produce a crosslinked polymeric network. In a multi-component system, the precursors react with each other to form a hydrogel. In embodiments, the precursors may be nucleophilic/electrophilic reactive components, such as succinimide and primary amines. In both the single and multi-component hydrogel systems, the hydrogel may crosslink with the osseous phase. In embodiments, the biopolymer component of the hydrogel may promote cell attachment and proliferation. In some embodiments, the hydrogel may contain proteins, peptides, and/or growth factors for promoting chondrogenesis.

Formulations may be prepared that are suited to make precursor crosslinking reactions occur in situ. In general, this may be accomplished by having a precursor that can be activated at the time of application to a tissue to form a crosslinked hydrogel. Activation can be made before, during, or after application of the precursor to the tissue, provided that the precursor is allowed to conform to the tissue's shape before crosslinking and associated gelation is otherwise too far advanced. Activation includes, for instance, mixing precursors with functional groups that react with each other. Thus, in situ polymerization includes activation of chemical moieties to form covalent bonds to create an insoluble material, e.g., a hydrogel, at a location where the material is to be placed on, within, or both on and within, a patient. In situ polymerizable polymers may be prepared from precursor(s) that can be reacted such that they form a polymer within the patient. Thus precursor(s) with electrophilic functional groups can be mixed or otherwise activated in the presence of precursors with nucleophilic functional groups.

In other embodiments, where electrophilic precursors are used, such precursors may react with free amines in tissue, thereby serving as a means for attaching the hydrogel to tissue.

The crosslinking reaction leading to gelation can occur, in some embodiments within a time from about 1 second to about 5 minutes, in embodiments from about 3 seconds to about 1 minute; persons of ordinary skill in these arts will immediately appreciate that all ranges and values within these explicitly stated ranges are contemplated. For example, in embodiments, the in situ gelation time of hydrogels according to the present disclosure is less than about 20 seconds, and in some embodiments, less than about 10 seconds, and in yet other embodiments less than about 5 seconds.

The osteochondral plug of the present disclosure promotes tissue repair in an osteochondral defect by filling the void of the lesion with a tissue specific scaffold which promotes its respective tissue regeneration. The osteochondral defect also promotes integration with a tissue void by form fitting the defect.

Embodiments of the present disclosure will now be described, by way of example only, with reference to the accompanying drawings.

Referring to FIG. 1, osteochondral plug 10 includes osseous phase 12 and chondral phase 14. Osseous phase 12 is a solid scaffold formed from a poly(lactic-co-glycolic acid) sponge modified to includes bone growth factors which are released into bone "b." The osseous phase 12 also contains free amines for bonding with the chondral phase 14. It is envisioned that portions of the osseus phase may also bond with bone "b" to enhance tissue integration. The chondral phase 14 is a hydrogel formed from PEG star and collagen precursors. The chondral phase 14 includes cartilage growth factors which are released into cartilage "c." In embodiments, the chondral phase 14 may be formed in situ and thus added to the tissue void containing the osseous phase 12 as a liquid. The liquid gels in situ thus filling any gaps that may form between the bone "b" and the osseous layer 12 of the osteochondral plug 10.

Figure 2:
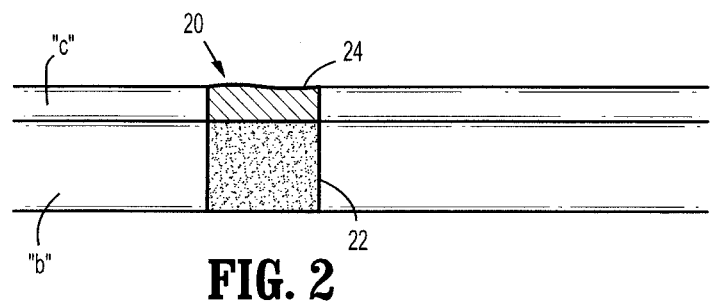
FIG. 2 schematically shows an osteochondral plug placed within an osteochondral defect in accordance with another embodiment of the present disclosure.

Turning now to FIG. 2, an osteochondral plug 20 includes osseous phase 22 and chondral phase 24. The osseous phase 22 is a soft, self-curing porous bone cement modified with free amines for covalently bonding with the bone "b" in which it is placed as well as for bonding with the chondral phase 24. Chondral phase 24 is a hydrogel formed from PEG star and collagen precursors. In embodiments, the bone cement is formed and added to the bone "b" as a slurry for curing in situ. The chondral phase 24 may be added to the tissue void in liquid form as described in FIG. 1 above, or may be pre-formed and placed within cartilage "c."

Figure 3:
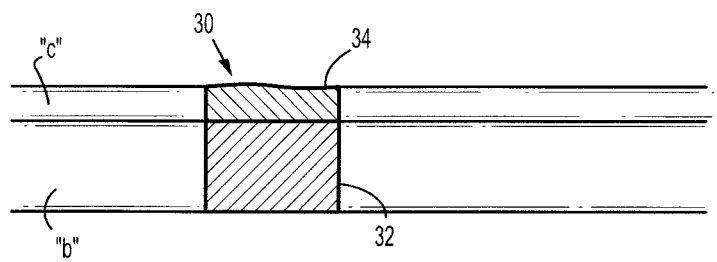
FIG. 3 schematically shows an osteochondral plug placed within an osteochondral defect in accordance with yet another embodiment of the present disclosure.

FIG. 3 illustrates an osteochondral plug 30 including an osseous phase 32 and a chondral phase 34. Both the osseous phase 32 and the chondral phase 34 are formed from a hydrogel containing NHS functionalized PEG star and collagen precursors, respectfully. The PEG star architecture of the osseous phase 32 and the chondral phase 34, as well as the concentration of the PEG star, are different thus altering the mechanical properties and gelation kinetics of each phase. As described above, variations of the molecular weight and chemistry of the biopolymer can also control the mechanical properties and gelation kinetics of a hydrogel. Additionally, these parameters can control the pore volume, release kinetics for biological materials (e.g., growth factors, DNA, etc.), and cellular response (e.g., migration). The hydrogel of the osseous phase 32 is in the form of a stiff gel and includes bone growth factors which are released into bone "b." The hydrogel of the osseous phase 32 may be introduced as a liquid into bone "b" and allowed to solidify before the introduction of the hydrogel of the chondral phase 34. The hydrogel of the chondral phase 34 may also be introduced in liquid form and may include cartilage growth factors which are released into cartilage "c."

Figure 4:
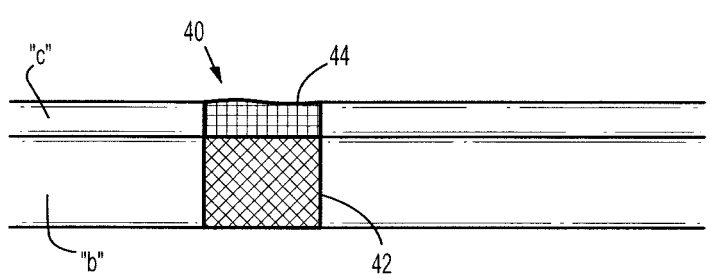
FIG. 4 schematically shows an osteochondral plug placed within an osteochondral defect in accordance with yet another embodiment of the present disclosure.

FIG. 4 illustrates an osteochondral plug 40 including a solid osseous phase 42 and a solid chondral phase 44. The osseous phase 42 is a solid scaffold formed from a poly (lactic-co-glycolic acid) sponge modified to include bone growth factors which are released into bone "b." The osseous phase 42 also contains free amines for covalently bonding with the bone "b" in which it is placed as well as for bonding with the chondral phase 44. The chondral phase 44 is a solid scaffold such as a collagen sponge with dry PEG star precursors disposed therein and thereon. Bioactive agents may also be added to the collagen sponge, such as cartilage growth factors. Upon placement of the solid chondral phase 44 within cartilage "c," the scaffold hydrates from contact with bodily fluids, such as blood, and the PEG star precursors react to form a gel. The gel can seal any gaps within the tissue void and can covalently bond the scaffold to the cartilage "c" as well as the osseous phase 42 of plug 40.

While biphasic embodiments are shown above, the osteochondral plug of the present disclosure may have more than two phases, each being formed from any of the variety of materials as described above, and including any of the bioactive agents as also described above.

Figure 5A:
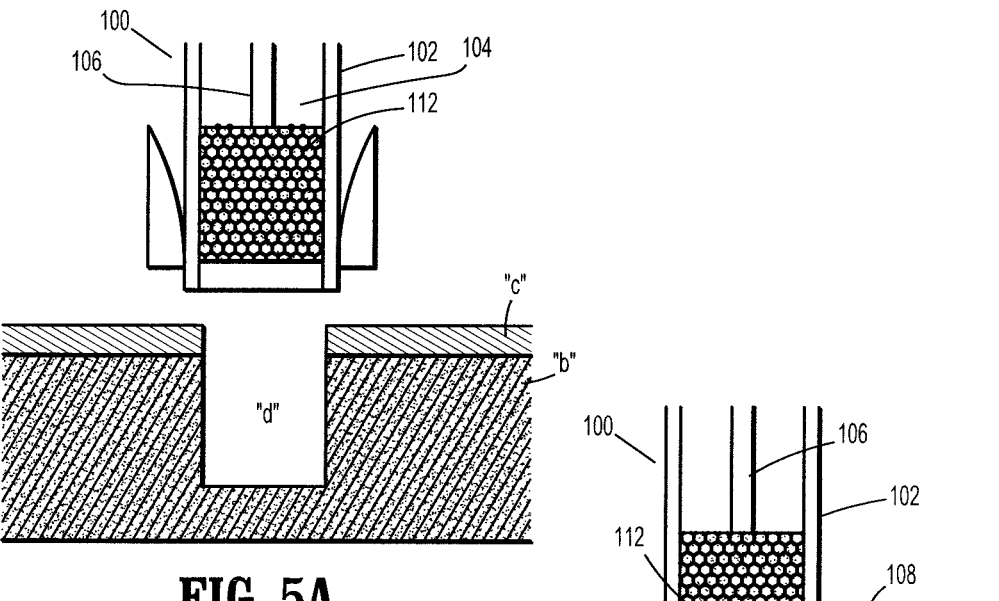
FIGS. 5A-5C schematically illustrate a method of inserting an osteochondral plug into an osteochondral defect in accordance with one embodiment of the present disclosure.
Figure 5B:
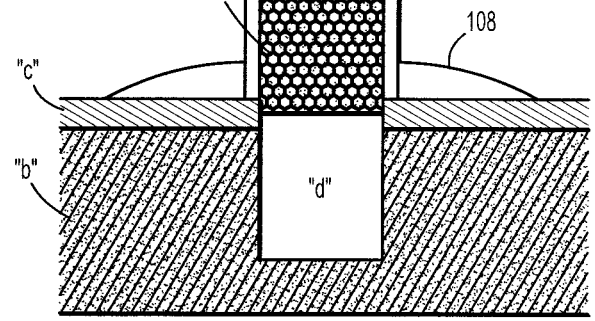
Figure 5C:
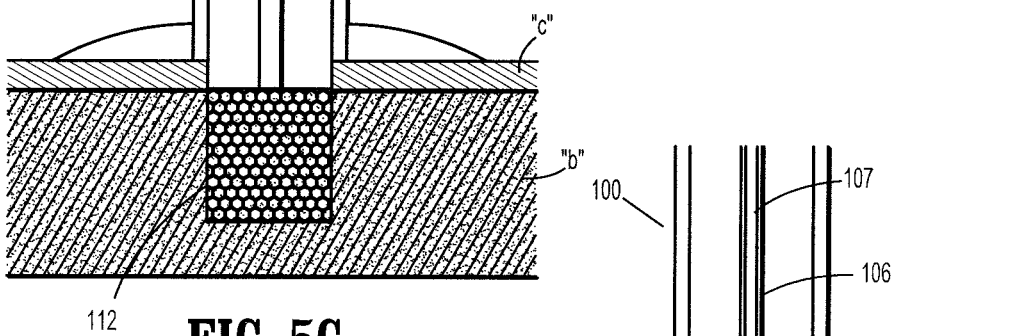
Figure 5D:
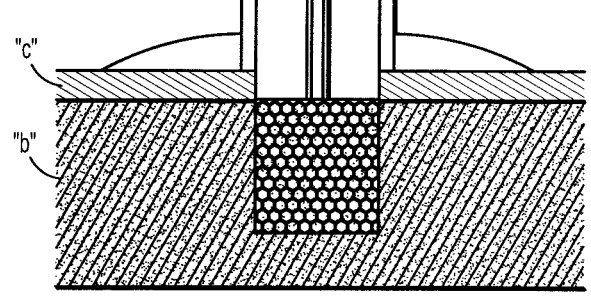

A method for implanting an osteochondral plug of the present disclosure is illustrated in FIGS. 5A-5D. Implantation of an osteochondral plug may be by way of open or minimally invasive surgery. After an osteochondral defect has been identified and cleaned, a delivery device 100, loaded with at least the osseous phase 112 of the osteochondral plug, may be placed over the defect "d" as illustrated in FIG. 5A. The delivery device includes an outer shaft 102 including an inner channel, or lumen, 104 housing the osseous phase 112 of the osteochondral plug. An inner shaft, or plunger, 106 is slidably engaged within the inner channel 104 of the outer shaft 102 for driving material disposed therein into defect "d." As illustrated in FIG. 5B, surface guides 108 are deployed to stabilize the device 100 against the tissue as well as to align the device with the defect "d." The osseous phase 112 is ejected from the outer shaft 102 of the delivery device 100 by advancing the plunger 106 in the direction of the defect "d." As described above, the osseous phase 112 may be in a solid or viscous form. Turning now to FIG. 5C, the osseous phase 112 fills the defect "d" up to the subchondral bone surface "b." After placement of the osseous phase 112, the plunger 106 is drawn back up into the inner channel 106 of the outer shaft 102 of the delivery device 100, at a level that may be substantially aligned with the cartilage surface "c." As illustrated next in FIG. 5D, the plunger 106 may include a central bore 107 through which the material of the chondral phase 114 may be passed to fill the remainder of the defect, i.e., cartilage "c." Thus, a hydrogel composition (chondral phase) may be introduced into the defect "d" through central bore 107 of plunger 106. The osteochondral plug is then allowed to cure and the delivery device 100 may be removed. Alternatively, plunger 106 may be removed from outer shaft 102 after placement of osseous phase 112 and the precursor(s), which may be placed into solution prior to use, may be delivered to the defect via a syringe (not shown). One may use a syringe for delivery of a single precursor, i.e., an electrophilic crosslinker, or a dual syringe or similar device to apply more than one precursor solutions, such as those described in U.S. Pat. Nos. 4,874,368; 4,631,055; 4,735,616; 4,359,049; 4,978,336; 5,116,315; 4,902,281; 4,932,942; 6,179,862; 6,673,093; and 6,152,943.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. Various modifications and variations of the osteochondral plug, the desired properties of the osseous and chondral phases, as well as methods of forming the osseous and chondral phases of the device and attaching the components together, will be apparent to those skilled in the art from the foregoing detailed description. Such modifications and variations are intended to come within the scope and spirit of the claims appended hereto.

What is claimed is:

1. An osteochondral implant comprising:
an osseous phase comprising a first scaffold comprising a first sponge comprising poly(lactic-co-glycolic acid) and having an outer surface containing one or more pendant reactive functional groups; and
a chondral phase comprising a second scaffold comprising a second sponge comprising collagen and having in and on the sponge at least one dry hydrogel precursor containing one or more pendant complimentary reactive functional groups capable of forming a bond with the one or more pendant reactive functional groups of the first scaffold,
wherein the first sponge further comprises bone growth factors and the second sponge further comprises cartilage growth factors.

2. The osteochondral implant according to claim 1, wherein the one or more pendant reactive functional groups comprise an electrophilic group.

3. The osteochondral implant according to claim 2, wherein the electrophilic group is selected from the group consisting of N-hydroxysuccinimides, sulfosuccinimides, carbonyldiimidazole, sulfonyl chloride, aryl halides, sulfosuccinimidyl esters, N-hydroxysuccinimidyl esters, succinimidyl esters, isocyanates, thiocyanates, carbodiimides, benzotriazole carbonates, epoxides, aldehydes, maleimides, imidoesters, and combinations thereof 4. The osteochondral implant according to claim 1, wherein the one or more pendant reactive functional groups comprise a nucleophilic group.

5. The osteochondral implant according to claim 4, wherein the nucleophilic group is selected from the group consisting of $-NH_2$, $-SH$, $-OH$, $-PH_2$, $-CO-NH-NH_2$ and combinations thereof.

6. The osteochondral implant according to claim 4, wherein the nucleophilic group is an amine group.

7. The osteochondral implant according to claim 4, wherein the one or more complimentary reactive functional groups comprise an electrophilic group.

8. The osteochondral implant according to claim 7, wherein the electrophilic group is selected from the group consisting of N-hydroxysuccinimides, sulfosuccinimides, carbonyldiimidazole, sulfonyl chloride, aryl halides, sulfosuccinimidyl esters, N-hydroxysuccinimidyl esters, succinimidyl esters, isocyanates, thiocyanates, carbodiimides, benzotriazole carbonates, epoxides, aldehydes, maleimides, imidoesters, and combinations thereof.

9. The osteochondral implant according to claim 2, wherein the one or more complimentary reactive functional groups comprise a nucleophilic group.

10. The osteochondral implant according to claim 9, wherein the nucleophilic group is selected from the group consisting of $-NH_2$, $-SH$, $-OH$, $-PH_2$, $-CO-NH-NH_2$ and combinations thereof.

11. The osteochondral implant according to claim 9, wherein the nucleophilic group is an amine group.

12. The osteochondral implant according to claim 1, further comprising at least one bioactive agent.

13. The osteochondral implant according to claim 12, wherein the bioactive agent is selected from the group consisting of amino acids, peptides, antibodies, enzymes, drugs, bone growth factors, bone morphogenic proteins, and combinations thereof.

* * * * *